US011282601B2

(12) United States Patent
Wu et al.

(10) Patent No.: US 11,282,601 B2
(45) Date of Patent: Mar. 22, 2022

(54) AUTOMATIC BOUNDING REGION ANNOTATION FOR LOCALIZATION OF ABNORMALITIES

(71) Applicant: International Business Machines Corporation, Armonk, NY (US)

(72) Inventors: Joy Tzung-yu Wu, San Jose, CA (US); Yaniv Gur, San Jose, CA (US); Alexandros Karargyris, San Jose, CA (US); Tanveer Fathima Syeda-Mahmood, Cupertino, CA (US)

(73) Assignee: International Business Machines Corporation, Armonk, NY (US)

( * ) Notice: Subject to any disclaimer, the term of this patent is extended or adjusted under 35 U.S.C. 154(b) by 137 days.

(21) Appl. No.: 16/840,877

(22) Filed: Apr. 6, 2020

(65) Prior Publication Data
US 2021/0313045 A1 Oct. 7, 2021

(51) Int. Cl.
*G06K 9/20* (2006.01)
*G16H 30/40* (2018.01)
(Continued)

(52) U.S. Cl.
CPC .......... *G16H 30/40* (2018.01); *G06K 9/6256* (2013.01); *G06N 20/00* (2019.01); *G06V 10/22* (2022.01); *G06V 2201/03* (2022.01)

(58) Field of Classification Search
CPC .............................. G16H 30/40; G06N 20/00
See application file for complete search history.

(56) References Cited

U.S. PATENT DOCUMENTS 5,633,511 A    5/1997  Lee et al.
10,606,982 B2  3/2020  Guo et al.
(Continued)

FOREIGN PATENT DOCUMENTS

WO    WO2019/136349 A2    7/2019

OTHER PUBLICATIONS

High, Rob, "The Era of Cognitive Systems: An Inside Look at IBM Watson and How it Works", IBM Corporation, Redbooks, Dec. 12, 2012, 16 pages.
(Continued)

*Primary Examiner* — Tuan H Nguyen
(74) *Attorney, Agent, or Firm* — Stephen J. Walder, Jr.; Kelsey Skodje

(57) ABSTRACT

Mechanisms are provided for automatically annotating input images with bounding region annotations and corresponding anomaly labels. The mechanisms segment an input image to generate a mask corresponding to recognized internal structures of a subject. A template data structure is generated that specifies standardized internal structure zones of the subject. The mechanisms register the mask with the template data structure to generate a template registered mask identifying standardized internal structure zones present within the mask, and generate bounding region annotations for each standardized internal structure zone of the template registered mask. The bounding region annotations are correlated with labels indicating whether or not the bounding region comprises an anomaly in the input image based on an analysis of a received natural language text description of the input image. The bounding region annotations and labels are stored in association with the input image.

18 Claims, 6 Drawing Sheets

(51) Int. Cl.
    G06N 20/00     (2019.01)
    G06K 9/62      (2022.01)
    G06V 10/22     (2022.01)

(56) References Cited

U.S. PATENT DOCUMENTS

| | | | |
|---|---|---|---|
| 2007/0168225 A1* | 7/2007 | Haider | G16H 10/20 |
| | | | 705/2 |
| 2018/0108124 A1 | 4/2018 | Guo et al. | |
| 2018/0137689 A1* | 5/2018 | Eastwood | G06T 15/08 |
| 2019/0026278 A1 | 1/2019 | Abedin et al. | |
| 2019/0332890 A1 | 10/2019 | Wang et al. | |
| 2020/0020107 A1 | 1/2020 | Kakrania et al. | |

OTHER PUBLICATIONS

Yuan, Michael J., "Watson and Healthcare, How natural language processing and semantic search could revolutionize clinical decision support", IBM Corporation, developerWorks, http://www.IBM.com/developerworks/industry/library/ind-watson/, Apr. 12, 2011, 14 pages.

"RSNA Pneumonia Detection Challenge", Kaggle, accessed online Apr. 22, 2020, 3 pages.

Coden, Anni et al., "SPOT the drug! An unsupervised pattern matching to extract drug names from very large clinical corpora", 2012 IEEE Second Conference on Healthcare Informatics, Imaging and Systems Biology, Sep. 27-28, 2012, 7 pages.

Irvin, Jeremy et al., "CheXpert: A Large Chest Radiograph Dataset with Uncertainty Labels and Expert Comparison", arXiv: 1901.07031v1 [cs.CV], Jan. 21, 2019, 9 pages.

Johnson, Alistair E. et al., "MIMIC-CXR-JPG, A Large Publicly Available Database of Labeled Chest Radiographs", arXiv:1901.07042v5 [cs.CV], Nov. 14, 2019, 7 pages.

Langlotz, Curtis P. et al., "A Roadmap for Foundational Research on Artificial Intelligence in Medical Imaging: From the 2018 NIH/RSNA/ACR/The Academy Workshop", Radiology, vol. 291, No. 3, published online Apr. 16, 2019, 12 pages.

Li, Zhe et al., "Thoracic Disease Identification and Localization with Limited Supervision", 2018 IEEE/CVF Conference on Computer Vision and Pattern Recognition, Jun. 2018, submitted version from arXiv: 1711.06373v6 [cs.CV], Jun. 20, 2018, 12 pages.

Lin, Tsung-Yi et al., "Focal Loss for Dense Object Detection", arXiv:1708.02002v2 [cs.CV], Feb. 7, 2018, 10 pages.

Lin, Tsung-Yi et al., "Keras RetinaNet", GitHub, Inc., accessed online Apr. 22, 2020, 9 pages.

Mettler, Jr., Fred A. et al., "Radiologic and Nuclear Medicine Studies in the United States and Worldwide: Frequency, Radiation Dose, and Comparison with Other Radiation Sources—1950-2007", Radiology, vol. 253: No. 2, Nov. 2009, 12 pages.

Moradi, Mehdi et al., "Bimodal network architectures for automatic generation of image annotation from text", 2018 International Conference on Medical Image Computing and Computer Assisted Intervention (MICCAI), submitted version from arXiv:1809.01610v1 [cs.CV], Sep. 5, 2018, 8 pages.

Rajpurkar, Pranav et al., "CheXNet: Radiologist-Level Pneumonia Detection on Chest X-Rays with Deep Learning", arXiv:1711.05225v3 [cs.CV], Dec. 25, 2017, 7 pages.

Ronneberger, Olaf et al., "U-Net: Convolutional Networks for Biomedical Image Segmentation", International Conference on Medical Image Computing and Computer-Assisted Intervention, Springer (2015), submitted version from arXiv:1505.04597v1 [cs.CV], May 18, 2015, 8 pages.

Shih, George et al., "Augmenting the NIH Chest Radiograph Dataset with Expert Annotations of Possible Pneumonia", Radiology: Artificial Intelligence, vol. 1, No. 1, published online Jan. 30, 2019, 12 pages.

Wang, Xiaosong et al., "ChestX-ray8: Hospital-scale Chest X-ray Database and Benchmarks on Weakly-Supervised Classification and Localization of Common Thorax Diseases", 2017 IEEE Conference on Computer Vision and Pattern Recognition (CVPR), Jul. 2017, submitted version from arXiv:1705.02315v5 [cs.CV], Dec. 14, 2017, 19 pages.

Yushkevich, Paul A. et al., "ITK-SNAP: an interactive tool for semi-automatic segmentation of multi-modality biomedical images", Conf Proc IEEE Eng Med Biol Soc., Aug. 2016, 11 pages.

Han, Changhee et al., "Learning More with Less: Conditional PGGAN-based Data Augmentation for Brain Metastases Detection Using Highly-Rough Annotation on MR images", Submitted on Feb. 26, 2019 (this version), latest version Aug. 22, 2019 (v5), arXiv:1902.09856v1 [cs.CV], Feb. 26, 2019, 8 pages.

Kovacik, Michal, "Organ Segmentation in 3D Medical Data Using Methods of Computer Vision", Master's thesis, Slovak University of Technology in Bratislava, Faculty of Informatics and Information Technologies, FIIT-182905-72174, Apr. 2019, 85 pages.

Le, Matthieu et al., "Computationally efficient cardiac views projection using 3D Convolutional Neural Networks", arXiv:1711.01345v1 [cs.CV], Nov. 3, 2017, 8 pages.

Li, Zhe et al., "Thoracic Disease Identification and Localization with Limited Supervision", Submitted on Nov. 17, 2017 (v1), last revised Jun. 20, 2018 (this version, v6), arXiv:1711.06373v6 [cs.CV], Jun. 20, 2018, 12 pages.

Schlemper, Jo et al., "Attention gated networks: Learning to leverage salient regions in medical images", Medical Image Analysis, vol. 53, Apr. 2019, 11 pages.

\* cited by examiner

AUTOMATIC BOUNDING REGION ANNOTATION FOR LOCALIZATION OF ABNORMALITIES

BACKGROUND

The present application relates generally to an improved data processing apparatus and method and more specifically to mechanisms for providing automatic bounding region annotation for localization of abnormalities.

Medical images, especially labeled (or annotated) images, are difficult and expensive to acquire. Often such labeled images require large expenditures of human effort and resources where a human subject matter expert (SME) must manually identify anatomical structures and characteristics within the medical images and annotate the medical images with identifiers of such anatomical structures and characteristics.

Machine learning algorithms may be trained to classify different medical conditions in medical imaging, such as identifying medical images with anomalies or diseases present in the medical images, and differentiating such medical images showing anomalies and diseases from normal medical images in which such anomalies are present. Such training often requires large sets of annotated or labeled medical images in order for the machine learning algorithm to reach convergence. Unfortunately, however, most sources of medical images provide the medical images as unlabeled or non-annotated medical images and, as mentioned above, the only current solution is to have SMEs manually annotate the medical images, which is not a viable solution.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided, in a data processing system comprising at least one processor and at least one memory, for automatically annotating input images with bounding region annotations and corresponding anomaly labels. The method comprises automatically segmenting an input image of a subject into one or more segments to generate a mask corresponding to recognized internal structures of the subject. The method further comprises generating a template data structure based on an input set of annotated images, wherein the template data structure specifies standardized internal structure zones of the subject. In addition, the method comprises automatically registering the mask with the template data structure to generate a template registered mask identifying standardized internal structure zones present within the mask. Furthermore, the method comprises automatically generating bounding region annotations for each standardized internal structure zone present in the template registered mask. Additionally, the method comprises automatically correlating the bounding region annotations with labels indicating whether or not the bounding region comprises an anomaly in the input image based on an analysis of a received natural language text description of the input image. The method also comprises automatically storing the bounding region annotations and labels in association with the input image to provide an automatically annotated and labeled image data structure.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein.

DETAILED DESCRIPTION

Figure 1A:
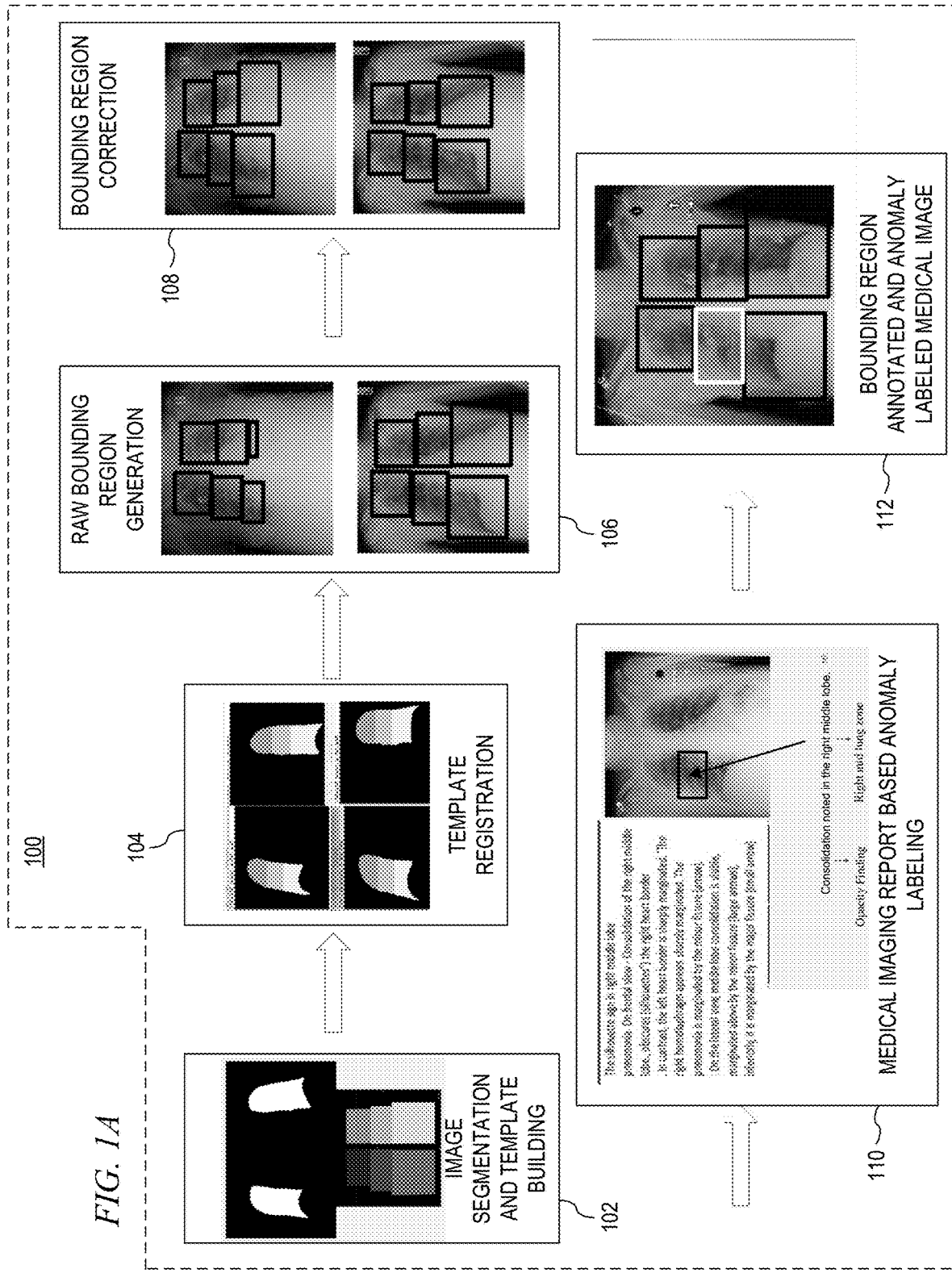
FIGS. 1A and 1B are example diagrams depicting the stages and primary computing elements of an automated medical image annotation and labeling (AMIAL) pipeline in accordance with one illustrative embodiment.

Automatic detection of findings, i.e. visually perceivable anomalies, and their locations in medical imaging studies, e.g., X-Ray imaging studies, CT scan imaging studies, etc., is an important research area for healthcare artificial intelligence, or cognitive computing, systems. Artificial intelligence systems that classify already identified anomalies are able to operate using image level labeling, however for the actual detection of the anomalies, and specifically the detection of the location of the anomalies in medical images, it is important to have bounding regions, e.g., bounding boxes or bounding polygons, that identify a subsection of the medical image where the anomaly is likely located.

This is because machine learning artificial intelligence systems operate based on sophisticated curve fitting algorithms and if they are trained with only image level labels (annotations), it is a much harder task to learn which pixels in the image correlate to the anomaly. One way to examine whether an artificial intelligence system, trained on image level labels, focused on the right area for prediction is to examine the activation map (last layer of the network) to figure out which pixels correlate most strongly with the final prediction. However, there are many cases where an artificial intelligence system, trained with weak image level labels, may guess the right answer but when one examines the activation map, one finds that the artificial intelligence neural network focused on completely irrelevant or clinically unreliable features for the classification/prediction. Also, without more localized bounding boxes (close to pixel level) annotation/ground truth, one cannot systematically assess whether the artificial intelligence system focused on the right areas for prediction for a large enough number of images to reach statistical conclusions.

The process of locally marking anomalies (findings) in medical images is both time consuming and costly as currently the process is a manual process that needs to be performed by specially trained medical imaging personnel, e.g., radiologists and the like. As touched upon above, to address this problem, weakly supervised approaches may be utilized to depict anomalies by looking at attention maps (last layer of a neural network) produced by convolution neural networks of artificial intelligence systems trained for anomaly classification. However, these approaches have not shown much promise so far and raised concerns whether the neural networks are actually focusing on the right abnormality regions of the medical images.

That is, with weakly supervised neural networks, the artificial intelligence neural network is trained with only image level labels such that the artificial intelligence (AI) neural network is trained with only the information that the image contains some abnormality but not where it is. The AI neural network thus, needs to learn the location of the abnormality and may not do so successfully, particularly in medical imaging, where the amount of information/pixels/voxels in the image can be very large but the actual abnormality area is very small. With bounding box level annotation, such as provided by the mechanisms of the illustrative embodiments as described hereafter, the supervision is "stronger" as the AI neural network knows more precisely where the pixels/voxels that matter for the classifications are during training and thus, the trained AI neural network is more likely to be reliable. In addition, one can assess the AI neural network's localization performance on the test set, which one cannot do with just image level "weak" labels.

To illustrate these issues with known methodologies, consider a chest X-ray (CXR), which is one of the most commonly requested radiography examinations in clinical practice, with over 100 million examinations ordered annually in the United States alone. In recent years, the open-sourcing of three large public CXR datasets with report-derived finding (anomaly) labels, have made the development of deep learning artificial intelligence (AI) algorithms for automatic global classification and detection of anomalies (findings) possible. However, while these datasets provide global finding labels for classification for all the images in the open source datasets, only small subsets of images have an additional manually generated marking of finding locations as bounding boxes, which are important for anomaly localization.

Due to this limitation, and the resources needed to build a large annotated dataset for localizing findings in terms of specially trained individuals and numbers of manhours, multiple attempts have been made to localize findings in a weakly-supervised manner using attention maps, such as described in Li et al., "Thoracic disease identification and localization with limited supervision," 2018 IEEE/CVF Conference on Computer Vision and Pattern Recognition, June 2018, pp. 8290-8299 and Rajpurkar et al., "Chexnet: Radiologist-level pneumonia detection on chest x-rays with deep learning," 2017. However, the radiology community is concerned about the reliability and interpretability of these algorithms, particularly whether these algorithms activated ("looked at") the relevant anatomical areas when making the classification.

To train better AI-based algorithms, the Radiology Society of North America (RSNA) commissioned a highly resource-intensive manual annotation effort for pneumonia related lung opacity in which 18 radiologists from 17 institutions annotated over several months to create a "gold standard" dataset of 30,000 CXRs with localized "bounding box" labels. This became a valuable dataset for the medical imaging community for developing anomaly localization machine/deep learning algorithms. However, the RSNA bounding box dataset has a few limitations. Firstly, the dataset is still relatively small in size for deep learning. There is also considerable inter-annotator variations in the lung area included in the opacity bounding boxes given the same CXR. Most importantly, the manual annotation effort and quality control steps cannot be scaled.

With the limitations of manual and AI anomaly (finding) classification mechanisms in mind, the illustrative embodiments described herein provide an improved automated computer tool that is specifically designed and specifically operates to perform computerized annotation of medical images with bounding regions for the localization of anomalies in medical images. The mechanisms of the illustrative embodiments provide an improved automated computer tool that is specifically designed and specifically operates to perform computerized annotation of medical images with these bounding regions and with anomaly labels, where the improved automated computer tool specifically leverages the medical imaging reports that accompany the medical images.

In some illustrative embodiments, the mechanisms of the illustrative embodiments, through a natural language processing and machine learning approach, learn the standard anatomical zones utilized by authors of medical imaging reports to specify the locations of anomalies (findings). In some illustrative embodiments, such standard anatomical zones may be provided as part of a knowledge database that maps anomalies to standard anatomical zones which may be constructed by subject matter experts (SMEs) or the like. The standard anatomical zones may be subsections or subregions of anatomical structures and may have various levels of specificity. For example, an anatomical structure that may be found through medical image segmentation is a right and/or left lung, which itself may be considered a standard anatomical zone. Moreover, the standard anatomical zones may further include specific regions within the lungs, e.g., upper, middle, and lower lung zones, if authors of medical imaging reports utilize such zone designations to identify locations of anomalies, or if such zones are generally known to be the locations of particular types of anomalies even if the zones are not specifically identified in the medical reports themselves, e.g., a pulmonary edema involves all zones of the lungs and thus, if a medical report indicates pulmonary edema, all zones of the lungs should be considered as regions of interest.

The illustrative embodiments implement these standard anatomical zones in the automated annotation of the medical image with corresponding bounding regions that identify the location of the anomaly in the medical image. The illustrative embodiments utilize the standardized anatomical regions and/or zones to map one or more medical imaging templates to the results of the medical image segmentation as part of an image registration operation, to thereby delineate the standard anatomical regions/zones in the segmentation results and thereby mark the standardized anatomical regions/zones on the target medical image. The marked regions/zones are then utilized as a basis for defining and annotating bounding regions in the original medical image. In still other illustrative embodiments, an automated bounding region correction mechanism and methodology are implemented to correct the dimensions of the bounding region based on predicted anatomical structure dimensions, such as when the automatically generated bounding region is misshapen due to opaque or non-discernable areas in the medical image causing the segmentation and registration to result in misshapen standardized anatomical regions/zones.

In some illustrative embodiments, a medical image labeling mechanism and methodology, that is anatomically standardized to the specific anatomical regions, e.g., upper, middle, and lower lung zones for the left and right lungs, is provided that is composed of two primary stages of computer artificial intelligence operation. In a first stage, medical image segmentation is performed, such as by using a convolutional neural network (e.g., UNet), deep learning model, or other artificial intelligence or cognitive computing model, and using one or more atlases of "normal" medical images to mark the anatomical zones of interest on the medical images with standardized bounding regions. It should be appreciated that an atlas, in the context of medical imaging and the present invention, is a set of medical images where regions of interest have been delineated by subject matter experts. Such sets of medical images provide information about the shape variations of the regions of interest as well as the pixel values, edges, and noisiness that may be expected in medical images with regard to these regions of interest. Moreover, a "normal" medical image is a medical image in which there are no anomalies present. The "normal" medical image is used with the medical image segmentation system, e.g., a convolutional neural network such as UNet, to train the medical image segmentation system to identify standardized anatomical zones.

As part of the first stage of operation, the medical image segmentation system generates a predicted mask of the anatomical structures of interest, e.g., the lungs in the running example that will be used herein, and a registration process is used to register a template of standardized anatomical zones to the predicted mask. In some illustrative embodiments, the masks are polygonal in shape and may have missing pixels. The template itself may be generated through a process of learning geometries of the standardized anatomical zones from manually annotated medical images. For example, the template may be generated by having a subject matter expert (SME) utilizes a manual tool, such as ITK-Snap or other image segmentation tool that permits manual delineation of anatomical structures, to specify a bounding region of one or more anatomical regions/zones corresponding to the mask. This may be done for a plurality of medical images in the atlas during a training operation, for example. The bounding regions for these anatomical regions/zones may be combined through a combinatorial algorithm to generate a template specifying bounding regions for the one or more anatomical regions/zones. For example, in one implementation, the dimensions of the geometries of the bounding regions for the plurality of medical images may be averaged across the plurality of medical images to generate a template.

The template is then registered with the segmentation results through an image registration process that predicts, for a medical image, the most likely coordinates of raw bounding regions using the segmentation output and the relative ratios from the bounding region examples used to define the template. That is, the template, specifies relative ratios of bounding region geometries based on a machine learning of these ratios from manually labeled training medical images.

The template based registration operation may involve using a deformable registration algorithm. Deformable registration algorithms generally operate to establish functional and/or spatial anatomical correspondences between different medical images, where the term "deformable" refers to the use of non-linear dense transformations, or a spatially varying deformation model, as opposed to linear or global deformation algorithms. Any known or later developed medical image registration algorithms may be used without departing from the spirit and scope of the present invention, however for purposes of illustration herein, the registration algorithm will be assumed to be a known deformable registration algorithm that is specifically adapted, however, to be applied to the annotated medical images having the bounding regions specified by the SME and specifically to generate a template of these annotated bounding regions.

Unlike conventional deformable registration algorithms that find correspondence between two images, the registration problem addressed here is fundamentally in that the specifically adapted registration algorithm of the illustrative embodiments registers a template, which specifies bounding regions of semantically marked regions, with an actual image. In other words, there is no image to image registration. Instead, the semantic constraints of the geometry and region identity are exploited. Specifically, a deep learning network is utilized that has been trained on prior medical images of manually marked anatomic structures to classify known anatomical structures (in the running example, the lungs). Then the known geometric constraints of the relative sizes of the various substructures and locations (in the example, the lower, upper, middle zones of the lungs) are imposed on the segmented structure using known structure features, e.g., the lung apex, as a reference point for correspondence. Using only the relative dimensions of the bounding regions for dividing up the anatomical structure regions/zones gives robustness to identifying the regions. Merging this with the region boundaries identified by the region segmentation operation gives automatically the corresponding anatomical structure regions/zones.

Thus, using the registration algorithm, the template image generated with bounding regions of one or more anatomical regions/zones corresponding to the masked anatomical structure identified based on a prediction of coordinates of the bounding regions determined from the learned ratios of geometry of the bounding regions learned through the registration process is registered with the segmentation results. For example, in the running chest x-ray lung image example, the 6 zones of the lungs, i.e. right upper, right middle, right lower, left upper, left middle, and left lower, are specified as bounding regions in the template image by annotated markings, such that this template may be applied to other medical images to identify these anatomical regions/zones of masked anatomical structures generated through the medical image segmentation operation. Hence, the template image specifies ratios of the geometry of the various standardized anatomical zones of interest to the particular type of medical image and/or anatomical structures, e.g., chest x-ray and lung structures, such that these ratios may be applied to other medical images to predict the locations of the standardized anatomical zones of interest in these other medical images and thereby annotate them for anomaly localization.

It should be appreciated that the medical image segmentation results, and thus, the registration of the bounding regions, may fail to properly identify anatomical structures and/or standardized anatomical zones where there is opacity in the medical image or other large abnormalities, as the underlying anatomical structures may not be visible. In such cases, the illustrative embodiments provide mechanisms that operate on the bounding regions specified by the segmentation and template based registration process discussed above, by applying standardized anatomical zone clinical heuristic algorithms that specify expected geometric relationships between anatomical characteristics and/or predicted bounding regions. The application of these standardized anatomical zone clinical heuristic algorithms essentially correct the shapes of the bounding regions based on expected geometries, and is referred to herein as a bounding region correction operation. The standardized anatomical zone clinical heuristic algorithms themselves are generated based on clinical observations and thus, are specific to the particular anatomical structures and standardized anatomical regions/zones of interest. Examples of such standardized anatomical zone clinical heuristic algorithms will be provided hereafter with regard to the running example of a chest x-ray and the anatomical structures of the lungs with the 6 standardized anatomical zones discussed previously. However, the invention is not limited to such and those of ordinary skill in the art will recognized in view of the present description that other standardized anatomical zone clinical heuristic algorithms can be generated for other anatomical structures and standardized anatomical regions/zones based on clinical observations without departing from the spirit and scope of the present invention.

As part of this bounding region correction operation, a quality control operation may be used to exclude a small number of medical images where the segmentation process failed to generate appropriate anatomical masks for use in generating the bounding regions through the registration and template based bounding region annotation process described above. For example, in some illustrative embodiments, if a particular predetermined number, or threshold number, of bounding regions are expected to be present in the template based annotated medical image having the bounding regions annotated on the medical image, and there is equal to or less than this particular predetermined number of bounding regions present in the annotated medical image, the annotate medical image may be excluded, e.g., if 6 lung zones are expected in the annotated medical images, a predetermined number or threshold number may be set to 4 such that if a medical image has equal to or less than 4 annotated standardized anatomical zones, the annotated medical image may be discarded from the bounding region annotated medical image dataset.

With the remaining bounding region annotated medical images, the bounding region correction operation uses expected proportions of bounding region geometries specified in the standardized anatomical zone clinical heuristic algorithms to modify the geometry of the raw bounding regions generated by the segmentation and registration process described previously, so as to correct the bounding regions in the finalized annotated medical images, i.e. the original medical images annotated with the bounding regions and anomaly labels. For example, in the case of bounding rectangles (often referred to as bounding boxes), the expected proportions of width and length may be utilized, and their relative position of elements of the geometries to each other, using ratios from across the whole dataset, to recalculate the bounding regions for each bounding region annotated medical image. This operation may be important for correcting the bounded anatomical region whenever there are obvious abnormalities that would cause the segmentation model built on normal anatomies to fail. Without this bounding region correction operation, in some cases the anatomical masks predicted by the normal atlas may include only the normal bounding region on the medical image and may fail to segment out the actual abnormality in the target anatomical region. If the loss of segmentation is due to segmentation error from the deep learning model used by the medical image segmentation system, particularly if the anomaly is the cause of the losses, this bounding region correction operation will allow the bounding regions to recapture the region of the anomaly.

In the second stage, the associated medical imaging report is used to label each standardized anatomical region/zone identified by the bounding regions, in the bounding region annotated medical image, as positive or negative for the corresponding anomaly (finding), resulting in a set of labeled bounding regions per medical image in the medical imaging study. That is, during the second stage, processing of medical imaging reports, based on an established modality specific vocabulary and set of medical concept to location mapping rules, and/or modality specific ontology that maps a discrete set of anomalies to a discrete set of possible anatomical locations that medical imaging professionals, i.e. subject matter experts (SMEs) might use to describe the location of the anomalies, is used to annotate labels for the various standardized anatomical regions/zones identified in the medical image. Moreover, natural language processing, based on the established vocabulary and/or ontology, may be performed on the medical imaging report to identify references to anomalies and determine which standardized anatomical zones these anomalies correspond to. In some cases, the medical imaging report may specify the particular location, e.g., "upper right lung", whereas in other cases, the anomaly instance may not specify the particular location. In the case that a location is not specifically identified in the medical imaging report, the medical concept, e.g., anomaly (finding), to location mapping rules may be utilized identify the locations with regard to standardized anatomical region/zone.

For example, in the case of a medical image depicting the lungs, the medical image segmentation system identifies the anatomical structures of the lungs within the medical image and generates a corresponding mask for each of the lungs. Through a registration process, the previously generated template for the standardized anatomical regions/zones of the lungs are identified and applied to the masks to generate modified masks having the standardized anatomical regions/zones (hereafter referred to simply as "zones") specified in the modified masked medical image. These standardized zones, for example, in the case of a lung medical image, may include the 6 standardized anatomical zones of the upper, middle, and lower right and left lungs identified. Thereafter, bounding regions in the original image are generated based on the modified masks to delineate the different standardized anatomical zones in the original image with annotations of the bounding regions.

Having identified the bounding regions of the standardized anatomical zones of the masked anatomical structures, the medical imaging report analysis mechanisms identify instances of references to anomalies in the text of the medical imaging report and identify the standardized anatomical zones corresponding to these identified instances of anomalies. The identified standardized anatomical zones are then labeled with corresponding labels as to the particular anomalies, if any, in the zones, or if the zone is does not include any anomalies labeling the zones as normal or non-anomalous, or not labeling those zones that do not include anomalies.

For example, in the example of the chest X-ray medical image and the lungs being the anatomical structure of interest, a modality specific ontology that maps a discrete set of abnormal findings to a discrete set of possible anatomical locations that radiologists might use to describe the location of the abnormal findings is obtained. The ontology is used in the natural language processing to extract both discrete abnormal findings (anomalies) and their discretized location from the natural language text radiology reports that come associated with each medical imaging study or examination. The discretized anatomical location is coordinated to match the bounding regions via the ontology for that radiology modality. The finding and location output of the natural language processing of each radiology report is used to label the associated bounding regions on the medical image as positive or negative for different abnormal findings (anomalies). In the case of negative findings, i.e. no anomaly present, in some illustrative embodiments the bounding region may not be reported in the bounding region annotated and labeled medical image generated as a result of the annotation and labeling process of the illustrative embodiments.

The final output of the segmentation, registration, bounding region correction, and medical report labeling pipeline (referred to herein overall as the automated medical image annotation and labeling (AMIAL) pipeline) of the illustrative embodiments is a fully labeled set of coordinates on an input medical image associated with presence or absence of target abnormal findings to aid training anomaly localization and classification artificial intelligence (AI) or cognitive computing systems. That is, the pipeline of the illustrative embodiments as described above, processes a plurality of medical images in a medical image dataset to thereby generate a dataset of medical images where the medical images are annotated with bounding regions and corresponding labels identifying abnormalities (findings or abnormal findings). This dataset is then input to an AI or cognitive computing system as a training dataset to thereby train that cognitive computing system to identify and classify anomalies. The dataset generated by the illustrative embodiments may operate as a ground truth labeled dataset against which the outputs of the AI or cognitive computing system may be evaluated to adjust, through a machine learning process, the operational parameters of the AI or cognitive computing system to minimize a loss (error) in the outputs generated by the AI or cognitive computing system. This training may utilize a supervised or unsupervised machine learning process.

Thus, the illustrative embodiments provide an improved automated computing tool mechanism and methodology that generates bounding region annotated medical images that are further labeled with anomaly labels that may be used to train AI or cognitive computing systems to perform anomaly identification and classification. The mechanisms of the illustrative embodiments greatly reduce reliance on manual efforts to perform medical image annotation and labeling for generating of training datasets, and further reduce errors due to variabilities in manual efforts for performing such training dataset generation. In one example experiment, the mechanisms of the illustrative embodiments automatically annotated a dataset of 13911 chest x-ray (CXR) images in a matter of hours, with an average annotation recall of 0.881 and precision of 0.896 when evaluated on 300 dual validated images. Moreover, the resulting bounding region annotated and labeled medical image dataset was used to train an opacity detection AI model using a RetinaNet architecture, and obtained anomaly localization results on par with the state-of-the-art.

Before continuing with the discussion of the various aspects of the illustrative embodiments in more detail, it should be appreciated that references to "annotating" and "annotation," in the context of the present description, refers to a process by which original data is augmented with additional data or metadata representing characteristics of the original data or results of analysis of the original data, so as to generate annotated data comprising the original data and the "annotations", i.e. the additional data representing the characteristics or results of analysis. In the context of the specific illustrative embodiments described herein, the annotating operations take original image data, represented as data structures, and add additional data or metadata to the original image data to identify bounding regions and labels, such as labels specifying locations of anomalies within the original image data, e.g., occlusions representing biological masses or the like. The annotating operations may include both manual and automatic annotation processes. For example, in some illustrative embodiments, a relatively small portion of an input dataset may be manually annotated by an SME using a computer tool to designate bounding regions for standard anatomical regions/zones so as to generate a template data structure that may be applied to a mask as part of a registration process as described previously. However, after having developed the template data structure, the template data structure may be utilized in an automatic annotation operation that automatically applies the template data structure to masks in other medical images to identify the standardized anatomical regions/zones and automatically generate bounding regions and corresponding labels in the manner previously described above.

In addition, it should again be appreciated that while example embodiments are described herein with regard to specifically chest x-ray medical images and human lungs as the anatomical structure of interest, the illustrative embodiments are not limited to such. To the contrary, the mechanisms of the illustrative embodiments are applicable to any modality of medical imaging, e.g., computed tomography (CT) scan, magnetic resonance imaging (MRI), ultrasound, etc.

Moreover, the mechanisms of the illustrative embodiments are applicable to any region of a subject and/or structure within the subject, and is not limited to the chest and lungs. It should be appreciated that the subject may be biological or non-biological, and in the case of a biological subject, may be a human, plant, animal, insect, or any other biological subject. In the case of other regions of a subject, and other types of subjects, the segmentation system is trained to perform segmentation specifically with regard to the particular type of subject and particular region of the subject and with regard to the particular internal structures of the subject. Moreover, the template data structures are developed for the particular masks generated by the segmentation system. The vocabulary and rules, or ontology, are developed for the specific subject and region of the subject for which the medical imaging is performed. The heuristic algorithms for correcting the bounding regions are generated based on observations regarding the relative geometries of the bounding regions. Thus, the mechanisms of the illustrative embodiments may be adapted to the particular subject, region, internal structures of interest, and observations of relative geometries of the bounding regions in similar subject images.

It should further be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 1B:
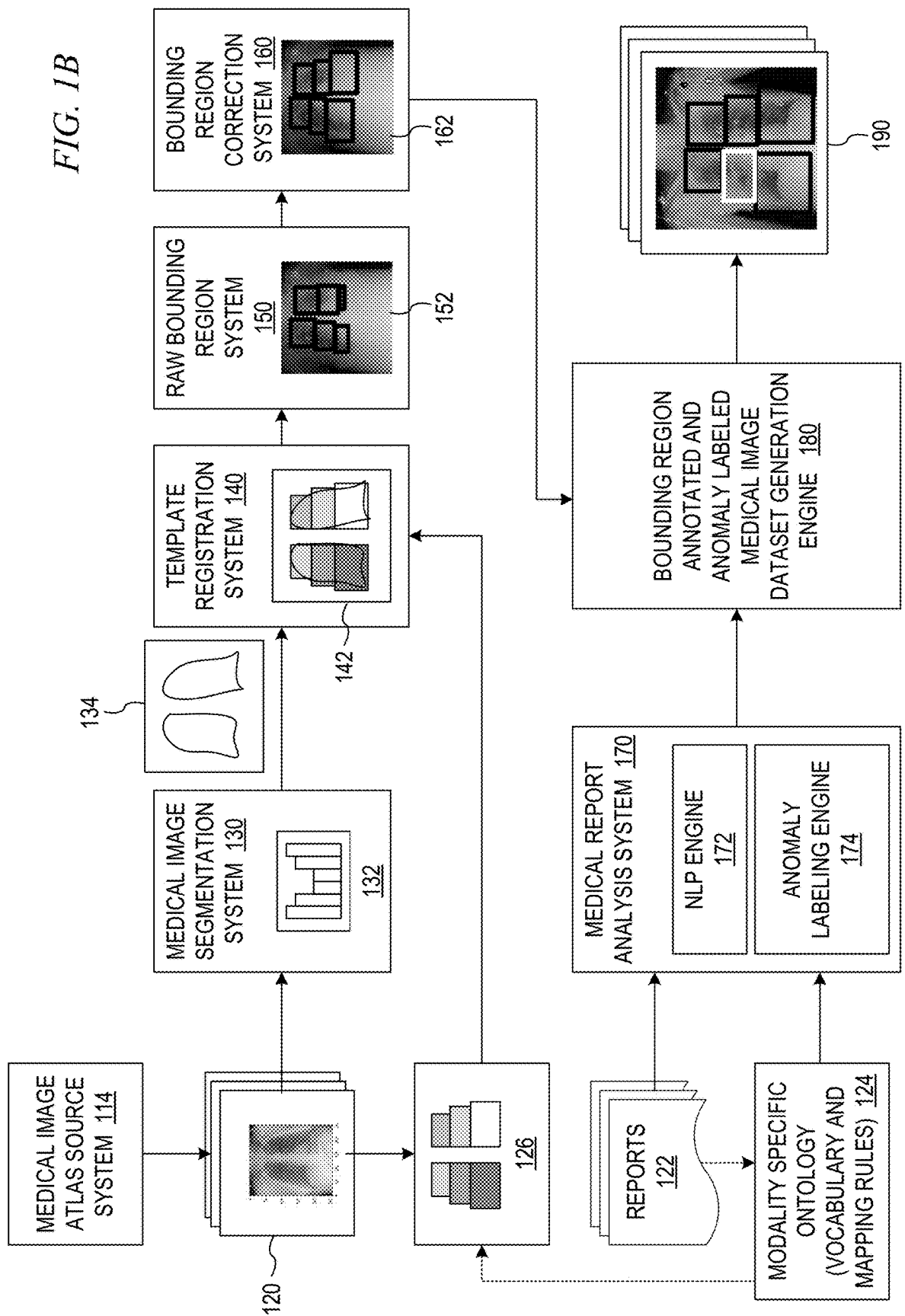

As noted above, the present invention provides mechanisms for providing automatic annotation of bounding regions and labeling of anomalies in medical images based on corresponding medical imaging reports so as to generate annotated medical images in which the locations of anomalies are specifically identified within he medical images. FIGS. 1A and 1B provide an example illustrative embodiment of the improved computing methodology of the automatic annotation process and improved computing tool mechanism elements that implement the automatic annotation process. FIG. 1A is an example data flow diagram showing the various stages of the computing pipeline for automatic annotation of medical images, while FIG. 1B shows a block diagram of the elements of the improved computing tool and computing pipeline used to implement the automatic annotation of medical images. These figures will be referenced together in the following description of the example illustrative embodiment.

As shown in FIGS. 1A and 1B, the improved computing tool and computing methodology of the illustrative embodiments includes a pipeline of mechanisms, referred to as the automated medical image annotation and labeling (AMIAL) pipeline 100 comprising a plurality of stages 102-112 of logic for performing the various improved computer functions described herein. Moreover, the AMIAL pipeline 100 comprises a plurality of computer models, artificial intelligence systems, data structures, and the like, as shown in FIG. 1B, to implement these specific improved computer functionalities. The AMIAL pipeline 100, overall, operates on non-annotated and non-labeled original medical images from a source system, and automatically annotates the original medical images with bounding regions and anomaly labels such that a bounding region annotated and anomaly labeled medical image is automatically generated. The resulting annotated and labeled medical image may be stored for later downstream use, e.g., such as in a medical image viewer, training an artificial intelligence system, or the like.

As discussed previously, in accordance with some illustrative embodiments, one goal of these illustrative embodiments is to automatically create a bounding region annotated and anomaly labeled medical image dataset 112 using an initial set of medical images 120, such as may be obtained from a publicly available medical image dataset source system 114, or the like, for example. Any source computing system, database, or the like, that is able to provide one or more medical image datasets for use with the mechanisms of the illustrative embodiments may be used, and it is not necessary for the medical images to be from a publicly available dataset source. For purposes of the ease of explanation hereafter, it will be assumed that the bounding regions are bounding "boxes", i.e. rectangles, but it should be appreciated that the bounding region may be any polygonal or other specific geometry based, or even free-form, region. Moreover, for purposes of illustration herein, it will be assumed that the initial set of medical images 120 is a set of National Institutes of Health (NIH), or other publicly available, medical image dataset, or subset thereof, available from a source computing system 114. The particular subset of the medical images obtained from the medical image atlas source system 114 may be specific to a particular type of subject (e.g., human subject) and internal region of the subject (e.g., chest). For example, using the running example of chest x-rays and lungs being the anatomical structures of interest, the initial set of medical images may be an NIH chest x-ray (CXR) dataset.

For this initial set of medical images 120, a corresponding set of medical imaging reports 122, as may be authored by medical imaging professionals, i.e. subject matter experts (SMEs), such as radiologist or the like, are also obtained. These medical imaging reports 122 comprise natural language text content in which the SME has presented their analysis of the corresponding medical image(s) 120 and may specify instances of anomalies and may specify, or may not specify, the particular location within the medical image 120 where the anomaly is located, referencing a standardized anatomical region/zone, e.g., "consolidation noted in the right middle lobe" where "consolidation" is the anomaly and "right middle lobe" is the standardized anatomical region/zone or location of the anomaly.

In addition, a vocabulary and set of medical concept to location mapping rules, and/or modality specific ontology 124 that maps a discrete set of anomalies to a discrete set of possible anatomical locations that medical imaging professionals, i.e. subject matter experts (SMEs) might use to describe the location of the anomalies. The ontology/vocabulary and rules may be generated in any suitable manner for the particular implementation. In some illustrative embodiments, the ontology and/or vocabulary and rules data structure(s) 124 may be manually generated by SMEs, such as in the form of a table data structure mapping medical concepts, such as anomalies, to a standardized set of anatomical locations. In other illustrative embodiments, a computer based natural language processing and statistical analysis of medical imaging reports may be performed to extract references to medical concepts and corresponding specifications of anatomical locations within the medical imaging reports, counts of the number of instances of pairs of medical concepts with anatomical locations may be maintained, and the counts may be evaluated to identify which specifications of anatomical locations are most often used by SMEs in their medical imaging reports such that these anatomical locations may be considered standardized anatomical locations. Any manner by which the ontology and/or vocabulary and mapping rules may be defined is intended to be within the spirit and scope of the present invention.

For purposes of the remaining operations of the AMIAL pipeline 100, it is assumed that the ontology/vocabulary and mapping rules, is provided as an input to the AMIAL pipeline 100 and provides a basis for mapping medical concepts to standardized anatomical locations in medical images of a given modality. For example, in the running example of the CXR and specifically the lungs, the ontology/vocabulary and mapping rules 124 comprises textual terms/phrases representing anomalies identified in the lungs and maps those anomalies to one or more of 6 standardized regions/zones of the lungs, i.e. upper, middle, and lower zones of the right and left lungs. That is, on frontal CXRs, the lungs can be divided into 6 non-overlapping "lung zones" that radiologists often refer to when describing lung abnormalities in CXR reports and thus, these 6 standardized regions/zones are utilized in the ontology/vocabulary and mapping rules 124.

As part of a first stage 102 of the AMIAL pipeline 100, the medical image segmentation system 130 receives one or more original medical images 120 from the medical image atlas source system 114, where these medical images have not yet been annotated with boundary region annotations or labeled with anomaly (findings) labels. It should be appreciated that in portions of this description where reference is made to a single medical image, the described operations are performed on one or more medical images. That is, individual medical images within the one or more medical images are processed by segmenting, registration, raw bounding region annotation generation, bounding region correction, and anomaly labeling, however in some cases operations are described with regard to a plurality of medical images. For example, the exclusion of medical images as part of a quality control operation during the bounding region correction stage 108 operations and the creation of a training set of annotated and labeled medical images in stage 112. With regard to these descriptions, it should be appreciated that the processing can be done individually for each individual medical image but that an atlas of a plurality of medical images may be processed in this manner to process and generate a dataset comprising a plurality of annotated and labeled medical images.

The medical image segmentation system 130 generates a predicted mask 134 of the anatomical structures of interest, e.g., the lungs in the depicted example. In some illustrative embodiments, the masks 134 are polygonal in shape and may have missing pixels, whereas in others illustrative embodiments, as depicted, the masks 134 comprise contours of various shapes matching the identified anatomical structures. As previously described above, in some illustrative embodiments, the medical image segmentation system 130 implements a trained UNet artificial intelligence computer model 132 to perform the medical image segmentation, although any other type of neural network, deep learning network, or machine learning trained artificial intelligence, or cognitive computing, system may be utilized. UNet is a specialized fully connected convolutional neural network (CNN) specifically developed by the computer Science Department of the University of Freiburg, Germany for performing biomedical image segmentation and thus, is used as a primary example of an artificial intelligence computer model used to perform segmentation, but the illustrative embodiments are not limited to such.

In one example implementation, using a UNet computer model 132, the UNet model was trained, through a machine learning training operation, using 150 "normal" or "no finding" frontal CXRs which were manually segmented for major anatomical structures, including the lungs. The trained UNet segmentation model was then used to predict separately the left and right lung segmentation masks for a plurality of other medical images in a given medical image dataset, such as the medical image dataset 120. To train the UNet computer model 132, the following UNet parameters were utilized: input shape=(256,256), base number filters=128, kernel size=3, dropout rate=0.5, learning rate=1e−3, optimizer=Adam, net depth=4, convolutions per depth=2, batch size=4, number batches per epoch=100, number of epochs=500. The DICE score (a statistical measure of similarity between the segmented mask and the ground truth annotated mask) on the left and right lungs were 93.7% and 96.9% respectively, in this example implementation.

After segmentation of the input medical image(s) 120, a template registration stage 104 is implemented in which one or more predefined templates 126 are applied to the masks 134 generated by the medical image segmentation system 130 to predict bounding regions of the masks 134 corresponding to the standardized anatomical zones represented in the templates 126. The templates 126 themselves are generated, for example as part of a template building process in stage 102, such as by having SMEs manually generate bounding regions on a selected subset of medical images of a same modality to thereby learn ratios of geometry of the bounding regions which can be used to predict coordinates of the bounding regions in other medical images. For example, in one implementation of the illustrative embodiments, without looking at the predicted lung mask generated in the image segmentation stage 102, a radiologist manually annotated all 6 standardized lung zones on 13 random normal frontal CXRs from the dataset 120. Each lung was divided into the upper, middle, and lower lung zones that typical radiologists would use to describe the location of lung abnormalities they see when reading CXRs. The radiologists marked a rectangular bounding box using a computer tool, such as ITK-Snap (an open source annotation computer tool), for example, to capture each lung zone completely. A combinatorial algorithm was applied to the set of 13 images to generate a template data structure 126 with a marking of the six lung regions as bounding boxes, such as by averaging the geometries of the manually generated bounding regions of the 13 images to thereby generate the template 126.

Thus, the template 126 comprises bounding regions corresponding to standardized anatomical zones of the anatomical structures of interest for the given medical imaging modality. It can be appreciated that different templates 126 may be generated for different modalities and different anatomical structures of interest and may be stored in a template database (not shown) for later retrieval and use in performing the automated bounding region annotation and anomaly labeling operations of the AMIAL pipeline 100. Thus, in some illustrative embodiments, a user may, as an input to the AMIAL pipeline 100, specify the anatomical structures of interest, e.g., lungs, heart, abdominal organs, and the medical imaging modality, e.g., frontal CXR medical images, and the corresponding template(s) 126 may be retrieved from the template database and provides as an input to the template registration system 140 of the AMIAL pipeline 100.

The template registration system 140, as part of the template registration stage 104 of the AMIAL pipeline 100, registers the mask 134 to the template 126 to generate the standardized anatomical zones mapped to the original input medical image 120 using the ratios of the geometry of the bounding regions specified in the template 126. For example, an adapted registration process may be utilized that registers the template 126 to the mask 134. The result is a template registered mask 142 that is provided to a raw bounding region system 150 that generates raw bounding region annotations in the original input medical image based on the template registered mask 142. That is, the raw bounding region system 150 predicts the coordinates for the contour boundaries of the standardized anatomical zones identified in the template registered mask 142, such as by using an affine transformation or the like, and thereby generates raw boundary region annotations 152.

Thus, for example, given a new target image, e.g., original medical image 120, for annotation, the left and right lung segmentations may be computed using the medical image segmentation system 130 and the UNet model 132, for example. Then, based on the lung segmentations, the medical image segmentation system 130 generates two bounding regions covering each of the lungs, which are referred to as the masks 134. These masks 134 are then used to register the template 126 to the original input medical image 120 and compute an affine transformation. The affine transformation is applied to the bounding regions of the template 126, e.g., the 6 bounding boxes for the standardized anatomical zones of the lung in the depicted example, to infer their coordinates on the original input medical image 120 and thereby generate the raw bounding boxes 152.

Figure 2A:
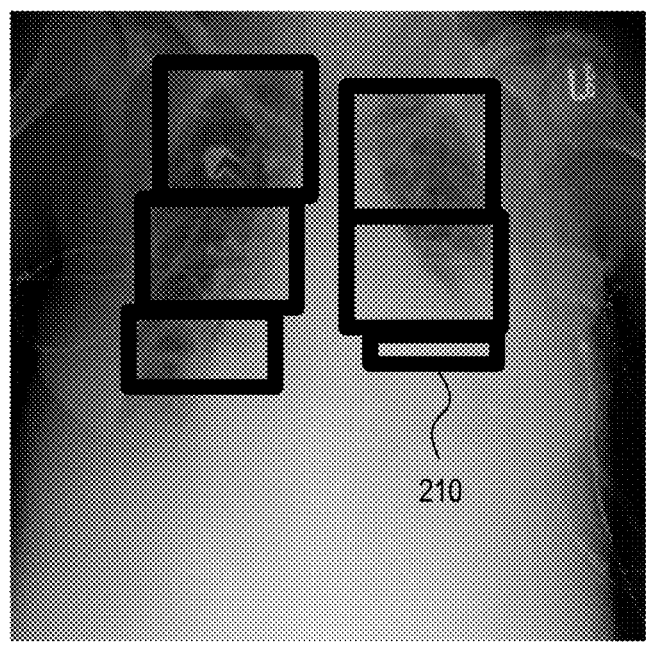
FIGS. 2A and 2B are example diagrams of medical images with bounding regions identified via automated bounding region annotation, and in which a correction of the bounding region is performed based on subject matter knowledge heuristics in accordance with one illustrative embodiment.

As noted previously, the medical image segmentation system 130 output, i.e. the masks 134, and thus, the registered raw bounding boxes 152 generated based on these masks 134, may fail to be accurate where there is marked opacity, occlusions, or other large abnormalities in the original medical image 120 making it difficult to identify anatomical structures within the original medical image 120. For example, as shown in FIG. 2A, because of opacity in the medical image, the lower zone of the left lung is not fully able to be discerned through segmentation 102 and registration 104. This results in a misshapen lower bounding region 210 for the left lung.

To improve the identification of the bounding regions within the input medical image 120, additional clinical heuristic algorithms may be applied by the bounding region correction system 160, as part of a bounding region correction stage 108 of the AMIAL pipeline 100. These additional clinical heuristic algorithms apply clinical intuitions and observations regarding expected relative geometries of the anatomical structures and bounding regions observed in practice, to the raw bounding regions 152 generated by the raw bounding region system 150. The clinical heuristics may specify particular portions of anatomical structures that are to be present in particular bounding regions and may specify features, or "clues", in the medical image that may be used as a basis for recalculating the bounding region coordinates when such features are discernable in the original medical image 120. Thus, by finding these clues in the medical image and correlating them with the raw bounding regions through the clinical heuristic algorithms, the bounding region coordinates may be recalculated and thereby corrected to represent the expected relative geometries of the bounding regions given the expected geometries of the anatomical structures. For example, in the CXR based example shown in FIGS. 1A and 1B, the standardized anatomical zone clinical heuristic algorithms of the bounding region correction system 160 are used to improve and derive the 6 final standardized bounding boxes for each CXR. To avoid missing lung anomalies (findings), the upper lung zones are expected to include the lung apices and the lower lung zones are expected to include the costophrenic angles.

Figure 2B:
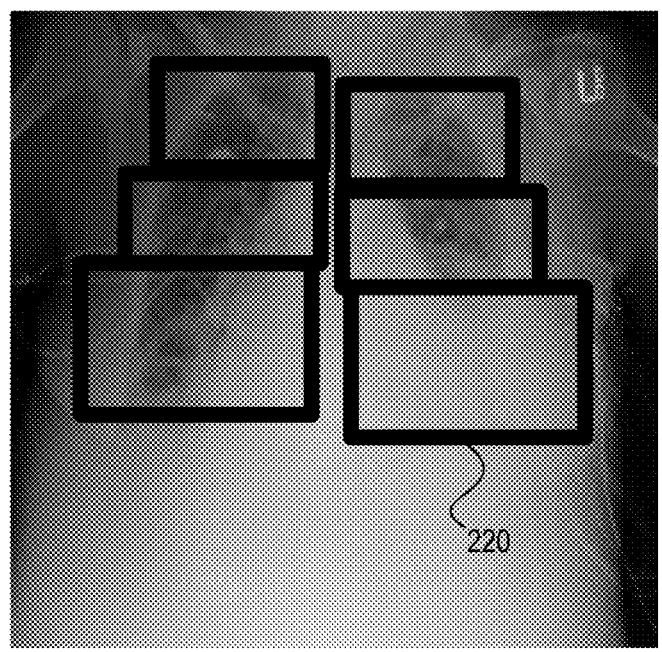

The application of these standardized anatomical zone clinical heuristic algorithms essentially correct the shapes of the raw bounding regions 152 based on the expected geometries when the raw bounding regions 152 do not comply with the expected geometries, such as due to misshapen raw bounding regions being generated because of anatomical structures were not able to be discerned during segmentation due to opacity, for example. The result is a corrected bounding region annotated medical image 162 in which the bounding regions comply with the expected geometries specified in the heuristic algorithms. For example, as shown in FIG. 2B, the misshapen bounding region 210 in FIG. 2A is corrected to have appropriate dimensions assuming an anatomical structure and correspondence between the anatomical structure that is identifiable in the medical image and the bounding regions, such that a corrected bounding region 220 is generated.

As part of the bounding region correction stage 108 operation performed by the bounding region correction system 160, a quality control operation may be performed to exclude a subset of medical images 120 where the segmentation process 102 failed to generate appropriate anatomical masks 134 for use in generating the bounding regions through the registration 104 and template based raw bounding region annotation process 106 described above. For example, in some illustrative embodiments, if a particular predetermined number, or threshold number, of bounding regions are expected to be present in the raw bounding region annotated medical images 152, and there is equal to or less than this particular predetermined number of bounding regions present in the annotated medical image, the annotate medical image may be excluded from later stages of processing and ultimately from inclusion in the set of bounding region annotated and anomaly labeled medical images 190 generated by the AMIAL pipeline 100.

For example, in the CXR example above, during the quality control operation of the bounding region correction 108 performed by the bounding region correction system 160, a small subset of the CXRs (e.g., 165 of an original 13911 medical images, or 1.2%) may be excluded for having less than 4 predicted raw bounding boxes. The segmentation stage 102 output generated by the medical image segmentation system 130 for these CXRs failed to identify enough of the lungs, which is usually due to large spinal devices, very poorly positioned patients, or lateral view CXRs (mistakenly labeled as frontal in the original dataset 120). In practice, these very difficult images would require a human-in-the-loop stage to draw the bounding boxes, but in the mechanisms of the illustrative embodiments, they are eliminated from further processing and inclusion in the final annotated and labeled medical image dataset 190.

For the remaining raw bounding region annotated medical images 152 that were not filtered out by the quality control operation, the bounding region correction operation executed by the bounding region correction system 160 uses expected proportions of bounding region geometries specified in the standardized anatomical zone clinical heuristic algorithms to modify the geometry of the raw bounding regions generated by the segmentation 102 and registration process 104, so as to correct the raw bounding regions in the finalized annotated medical images 112, 190, i.e. the original medical images annotated with the bounding regions and anomaly labels. These bounding region correction operations use clinically determined heuristics that tie expected medical image anatomical features to standardized anatomical zones and specify expected geometries such that the coordinates of bounding regions may be recalculated based on the raw bounding regions and the adjustments specified by the ratios and positioning of the bounding regions relative to expected medical image anatomical features. The result is a corrected annotated medical image 162 in which the raw bounding regions are corrected where necessary to generate final corrected bounding region annotations of the original medical image.

For example, with the CXR example, clinicians have determined that the upper lung zones tend to be the most reliably captured by the segmentation stage 102 output, particularly if marked lung opacity is present. Moreover, the left and right lungs have an expected geometry with regard to each other. Following this clinical intuition encoded into a set of standardized anatomical structure clinical heuristic algorithms, the coordinates of each lung zone are recalculated given the clues from the raw bounding boxes generated by the registration process 104 and raw bounding region stage 106.

For example, in one implementation of the illustrative embodiments, the clinical heuristic algorithms of the bounding region correction system 160 first realign the coordinates of the middle and lower lung zone bounding boxes of the right and left lungs to be closer to the coordinates of the corresponding upper lung zone bounding boxes. This results in a more consistent angle between the vertical and a line drawn through the centroids of all 3 lung zones on each side. Then, for each medical image 152 in a plurality of such medical images 152, the maximum height of the entire left or right lungs is obtained from the range between the highest and lowest point of the raw bounding regions. The average height proportions between the upper, middle, and lower lung zones from across the entire dataset 120 is then used to re-divide up each lung into 3 standardized zones vertically. Similarly, once the bounding region centroids are horizontally and vertically realigned, the average width of each lung zone is separately used to determine the sizes of each bounding region. As a result, the standardized bounding boxes correction performed in this manner assists in capturing the anatomical lung zones irrespective of lung abnormalities.

Having generated the final bounding region annotated medical images 162, labeling of anomalies relative to these bounding regions is performed using the medical imaging reports 122 associated with the medical images and the predefined modality specific ontology, and/or vocabulary and mapping rules resources 124. That is, the medical report analysis system 170, as part of the medical imaging report based anomaly labeling stage 110 of the AMIAL pipeline 100, performs natural language processing of on the medical imaging reports 122 based on the ontology/vocabulary and mapping rules 124, to extract instances of natural language terms/phrases referencing anomalies (findings) and anomaly locations, if such locations are specified in the reports 122. In cases where the locations are not specified in the reports 122 themselves, the modality specific ontology and/or mapping rules may be utilized to determine a default location for the referenced anomalies. That is the ontology and/or the mapping rules may correlate anomalies with standardized anatomical zones and these correlations may be used to map references to anomalies in natural language text to standardized anatomical zones corresponding to the bounding regions of the annotated medical images 162.

Thus, in the CXR example described above, the medical report analysis system 170 utilizes a CXR ontology that organizes CXR anomalies (findings) by discrete anatomical locations with which the findings could possibly be described by radiologists in reports. Lexical and semantic variants of descriptions of different anomalies (findings) and anatomical locations are bottom-up curated from a large corpus of CXR reports using a concept expansion tool. The vocabulary is validated by a selected set of radiologists to ensure high recall and precision.

Moreover, in the CXR example, an anomaly (finding) type to location mapping rule set is provided as a table formatted file where clinicians encode their knowledge of the most likely discrete bounding box anatomical locations of different anomalies. Again, this is important particularly in the "no mention of location" cases where the medical imaging report itself does not specify the location as the location is implied or generally understood by SMEs based on the identification of the anomaly. For example, the anatomical location of pulmonary edema is hardly ever described by radiologists in the medical imaging report because, by definition from the pathological processes for pulmonary edema, it is known that pulmonary edema is most likely to be distributed across all 6 standardized lung zones. Most importantly, any localization algorithm should assess all 6 lung zones in the case of predicting opacity from pulmonary edema.

Given the ontology and/or vocabulary and mapping rule set 124, and a medical imaging report 122, the natural language processing (NLP) engine 172 of the medical report analysis system 170 extracts from each portion of natural language content, e.g., sentence, both the anomaly references (findings) mentioned in an affirmative context and the associated discrete anatomical locations, e.g., lung zone location(s). Then the anomaly labeling engine 174 generates a corresponding anomaly label, e.g., opacity label, for each discrete standardized anatomical zone, e.g., lung zone, from the text output and merges the generated anomaly label with the corresponding standardized bounding region coordinates output from the bounding region correction system 160 to give the final more localized anomaly label annotations for the medical image, e.g., the more localized lung opacity labels. For example, if the text indicates that there is "consolidation noted in the right middle lobe", the reference to the location "right middle lobe" is mapped to the right middle zone bounding region in the annotated medical image 162 and the corresponding label for "consolidation" is generated and associated with the right middle zone bounding region in the annotated medical image 162. This results in the final annotated and labeled medical image generated in bounding region annotated and anomaly labeled medical image stage 112 of the AMIAL pipeline 100. In this final annotated and labeled medical image some of the bounding regions may include labels for annotations, some bounding regions may have labels indicating normal or non-anomalous states, bounding regions where there is no corresponding anomalous label may be eliminated, or any other desirable modification to the annotations may be made so that bounding regions with anomalous labels are indicated in a manner that emphasizes these bounding regions relative to non-anomalous bounding regions in the final annotated and labeled medical images 190.

As discussed previously, this final annotated and labeled medical image dataset 190 may be stored for later use by an AI or cognitive computing system. For example, in some implementations, the above AMIAL pipeline 100 mechanisms may be used to generate annotated and labeled medical images for viewing via a medical image viewer computing system so that a human user, e.g., radiologist or the like, may view the annotated and labeled medical images to thereby quickly identify anomalous regions of the medical image. In such a case the medical image viewer will render the annotated and labeled medical image in a graphical user interface where the bounding regions are displayed in a manner such as shown in FIGS. 1A-2B, for example, with appropriate characteristics to emphasize anomalous bounding regions, e.g., different colors, brightness, highlighting, or the like. For example, in one illustrative embodiment, the outline of a bounding region having a corresponding label indicating that the bounding region is positive for an anomaly (finding) may be displayed in a red color while other bounding regions that are not positive for anomalies may have a black, blue or other less conspicuous coloring. Moreover, labels may be displayed.

In still other illustrative embodiments, the annotated and labeled medical images 190 may be used as a training dataset for training other downstream AI and cognitive computing systems. For example, the dataset 190 may be used as a training dataset for machine learning training of an AI or cognitive computing system designed to perform medical image analysis, such as anomaly detection and location in non-annotated and non-labeled medical images. In such a case, a first portion of the dataset 190 may be utilized for training, a second portion may be utilized for validation, and a third portion may be utilized for testing. Any suitable supervised or non-supervised machine learning process may be implemented to actually train the AI or cognitive computing system, using the training dataset 190 generated by the mechanisms of the illustrative embodiments.

Thus, the illustrative embodiments provide improved computer tools and improved computer methodologies that automatically annotate and label medical images based on standardized anatomical regions/zones and are able to correct the resulting bounding regions based on expected geometries and expected correspondence between medical image features and the standardized anatomical regions/zones. Moreover, the mechanisms of the illustrative embodiments provide the ability to extract anomaly labels from medical imaging reports and correlate these labels with the automatically generated bounding region annotations to thereby automatically generate annotated and labeled medical images. The resulting automatically generated annotated and labeled medical images may be provided as a training dataset to perform training of AI and cognitive computing systems thereby reducing the required amount of resource costs for compiling large sets of annotated and labeled medical images as well as reducing manual efforts and significantly reducing errors due to reliance on manual efforts and variability in such manual efforts.

In addition, it can be appreciated that the mechanisms of the illustrative embodiments not only locally label abnormalities but also actually labels whether each standardized anatomical zone is normal or not. This is potentially very useful annotation/database for similarity based models. Moreover, one direct benefit from the AMIAL pipeline is that the AMIAL pipeline has in effect structured both the text in the medical imaging report and the medical image, which comports with professional society recommendations, such as the radiology society of north America (RSNA) which is a strong proponent of such technologies for improving the efficiency/quality/standardization of reporting.

Figure 3:
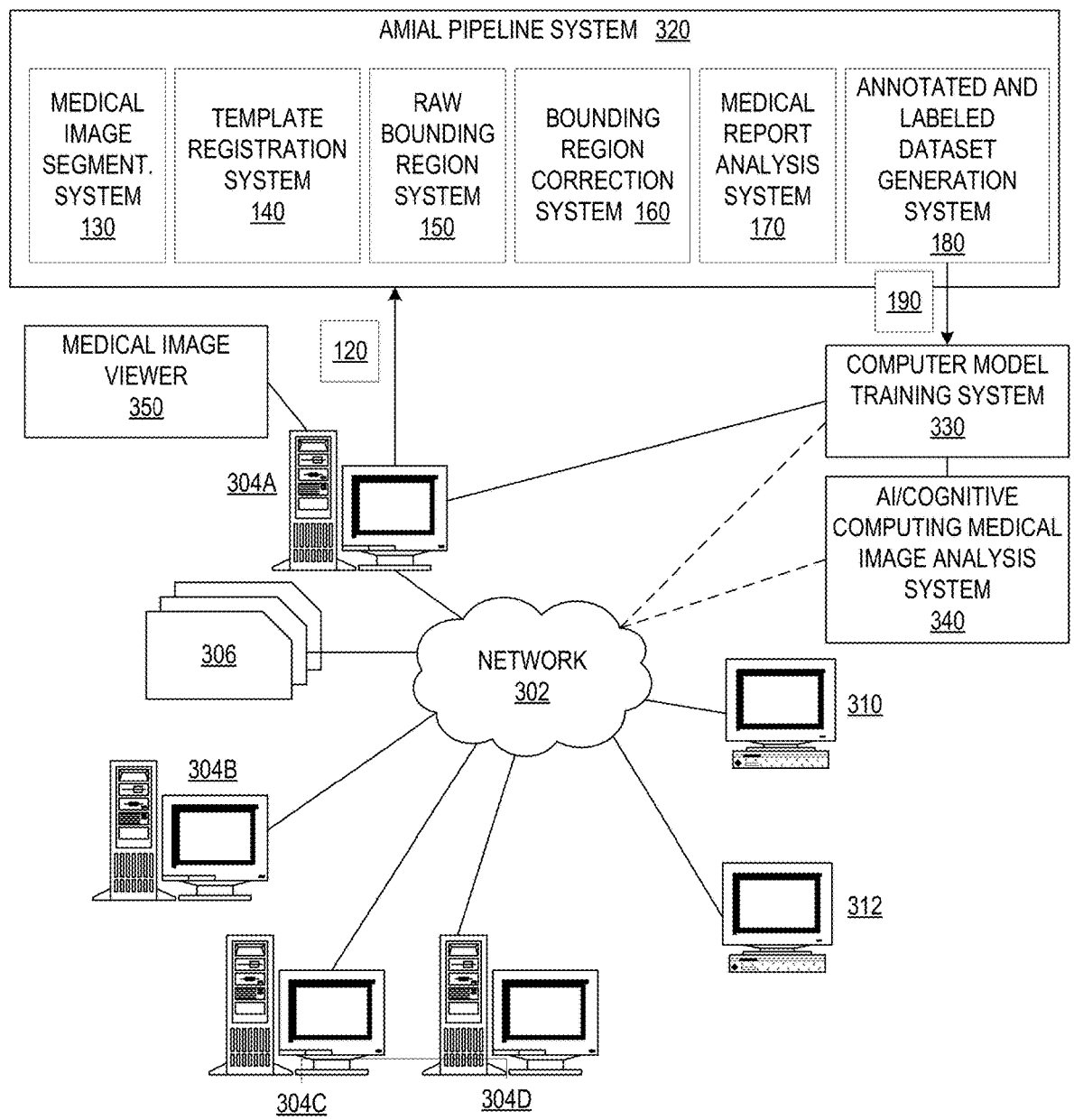
FIG. 3 depicts a schematic diagram of a cognitive medical image analysis system in a computer network in accordance with one illustrative embodiment.

FIG. 3 depicts a schematic diagram of a cognitive medical image analysis system in a computer network in accordance with one illustrative embodiment. As shown in FIG. 3, the automatic medical image analysis and labeling (AMIAL) pipeline system 320 is implemented on one or more computing devices 304A-D (comprising one or more processors and one or more memories, and potentially any other computing device elements generally known in the art including buses, storage devices, communication interfaces, and the like) connected to the computer network 302. For purposes of illustration only, FIG. 3 depicts the AMIAL pipeline system 320 being implemented on computing device 304A only, but as noted above the AMIAL pipeline system 320 may be distributed across multiple computing devices, such as a plurality of computing devices 304A-D. The network 302 includes multiple computing devices 304A-D, which may operate as server computing devices, and 310-712 which may operate as client computing devices, in communication with each other and with other devices or components via one or more wired and/or wireless data communication links, where each communication link comprises one or more of wires, routers, switches, transmitters, receivers, or the like.

In some illustrative embodiments, the AMIAL pipeline system 320 and network 302 enables a medical image annotation and labeling functionality for one or more users via their respective computing devices 310-312. For example, a user of a client computing device 310 may log onto server 304A to request that the AMIAL pipeline system 320 generate a set of automatically annotated and labeled medical images for training an instance of an AI or cognitive computing medical image analysis system 340. The user may specify the modality of the medical images to be utilized, the anatomical structures of interest, and/or any other parameters for performing the automatic annotation and labeling of medical images to generate a set of annotated and labeled medical images 190 for use by the computer model training system 330 to train an instance of the AI/cognitive computing medical image analysis system 340.

In other embodiments, the AMIAL pipeline system 320 and network 302 may provide other types of AI/cognitive operations including, but not limited to, request processing and cognitive response generation which may take many different forms depending upon the desired implementation, e.g., cognitive information retrieval, training/instruction of users, cognitive evaluation of data, such as medical imaging data, or the like. For example, in another illustrative embodiment, the server 304A may provide a medical image viewer application 350 which may be used by a user of client computing device 310 to access a medical imaging study comprising a plurality of medical images. In response to the user requesting access to the medical imaging study via the medical image viewer application 350, the AMIAL pipeline system 320 may be automatically employed to automatically retrieve the medical image study and annotate and label the medical images as part of a process for displaying, in the medical image viewer application 350, the annotated and labeled medical images with bounding regions and corresponding labels based on the AMIAL pipeline analysis of the medical image(s) and analysis of the corresponding medical imaging report. In automatically employing the AMIAL pipeline system 320, the metadata of the medical imaging study may be used to determine the modality of the medical imaging study as well as the principle anatomical structures for generating the masks and retrieving appropriate templates for performing the template registration. Moreover, such identification may be used to retrieve corresponding clinical heuristic algorithms and execute them to perform the bounding region correction in implementations where the AMIAL pipeline system 320 may be employed for various modalities and anatomical structures of interest.

It should be appreciated that the medical images themselves may be obtained from source computing systems remotely located from the computing system(s) 304A-304D on which the AMIAL pipeline system 320 is implemented. For example, a computing system may be coupled to the network 302 and associated with an organization providing a publicly available medical image dataset for general use. For example, 306 in FIG. 3 may represent a network attached storage system in which a publicly available dataset of medical images, e.g., the NIH dataset mentioned previously, is provided. The AMIAL pipeline system 320 may access such remotely located medical image datasets and utilize them, or a subset of them, as an original input medical image dataset for automatic generation of annotated and labeled medical images. Moreover, in other illustrative embodiments, computer systems, such as server 304D for example, may be associated with medical imaging organizations, hospitals, doctor offices, or any other source of medical images, where the medical images may be provided to the AMIAL pipeline system 320 for annotation and labeling in accordance with the illustrative embodiments described previously.

In some illustrative embodiments, the AMIAL pipeline system 320 may be employed by a cognitive computing system configured to implement a request processing pipeline that receives inputs from various sources. The requests may be sent from client computing devices 310-312, and may be posed in the form of a natural language question, natural language request for information, natural language request for the performance of a cognitive operation, or the like. For example, the cognitive system may receive input routed through the network 302, a corpus or corpora of electronic documents, such as from network attached storage 306, cognitive system users, and/or other data and other possible sources of input. Some of the computing devices 304A-D may include devices for a database storing the corpus or corpora of data comprising medical image datasets. The network 302 includes local network connections and remote connections in various embodiments, such that the cognitive system may operate in environments of any size, including local and global, e.g., the Internet.

The request processing pipeline of the cognitive system may comprise a plurality of stages for processing an input question/request based on information obtained from the corpus or corpora of data 306 and/or 340. For example, a doctor may input a question of the type "Where is the anomaly in Patient A's chest X-ray?" or may input a request of the type "Identify the anomaly in Patient A's chest X-ray." Alternatively, the question/request may be the selection, via a user interface of the like, of a particular operation to be performed by the cognitive system on a particular viewed medical image, such as may be viewed via the medical image viewer application 350. For example, the doctor may access a medical image associated with a patient and select an option to identify any anomalous regions in the medical image.

The cognitive system executing on the server 304A, and operating in conjunction with the AMIAL pipeline system 320, may generate answers/responses for the input question or request based on the processing of the input question/request and the corpus or corpora of data 306, 340. For example, the request to render the medical image, or to identify an anomalous region in the medical image, may invoke the operation of the AMIAL pipeline system 320 of the illustrative embodiments. Alternatively, the operation of the AMIAL pipeline system 320 of the illustrative embodiments may be performed automatically in response to new medical imaging data and corresponding electronic medical report documents being received. In the latter case, the cognitive system may perform a retrieval operation from the corpus of the already automatically annotated medical image data for performance of cognitive operations and/or rendering of the medical images via the medical image viewer application 350 with anomalous regions being depicted in accordance with the AMIAL pipeline system 320 operations described previously.

In some illustrative embodiments, the cognitive system may be the IBM Watson™ cognitive system available from International Business Machines Corporation of Armonk, N.Y., which is augmented with the mechanisms of the illustrative embodiments described herein. More information about the pipeline of the IBM Watson™ cognitive system may be obtained, for example, from the IBM Corporation website, IBM Redbooks, as well as in Yuan et al., "Watson and Healthcare," IBM developerWorks, 2011 and "The Era of Cognitive Systems: An Inside Look at IBM Watson and How it Works" by Rob High, IBM Redbooks, 2012.

In an example illustrative embodiment in which the mechanisms of the AMIAL pipeline system 320 are employed to generate a training dataset for training an AI/cognitive computing medical image analysis system 340, as shown in FIG. 3, an input dataset of medical images 120 is provided to the AMIAL pipeline system 320, such as by retrieval from one or more computing systems and/or storage systems coupled to the network 302. Thereafter, the elements of the AMIAL pipeline system 320 previously described above with regard to FIGS. 1A-1B operate on the input dataset 120 to generate a final annotated and labeled medical image dataset 190. That is, the medical image segmentation system 130, for each medical image in the input dataset 120, segments the medical image to generate the masks which are input to the template registration system 140 that registers the masks with the appropriate templates to generate the template registered masks that are input to the raw bounding region system 150. The raw bounding region system 150 generates raw bounding regions based on the template registered masks which are then input to the bounding region correction system 160. The bounding region correction system 160 applies appropriate clinical heuristic algorithms and quality control operations to generate corrected boundary regions in the medical images to generate a final set of bounding region annotations for the medical images. The medical report analysis system 170 performs NLP operations and anomaly labeling operations to correlate anomalies specified in the medical imaging reports with the final set of bounding region annotations. The annotated and labeled dataset generation system 180 then generates the final set of medical images 190 with the final bounding region annotations and corresponding anomaly labels that is output to the computer model training system 330.

The computer model training system 330 takes the final annotated and labeled medical image dataset 190 and uses it to train an instance of the AI/cognitive medical image analysis system 340. This may involve separating the dataset 190 into a training set, a validation set, and a testing set. Moreover, it should be appreciated that the computer model training system 330 and/or the AI cognitive computing medical image analysis system 340 may be provided on different computing systems coupled to the network 302, from each other and/or from the computing system 304A on which the AMIAL pipeline system 320 is implemented.

Figure 4:
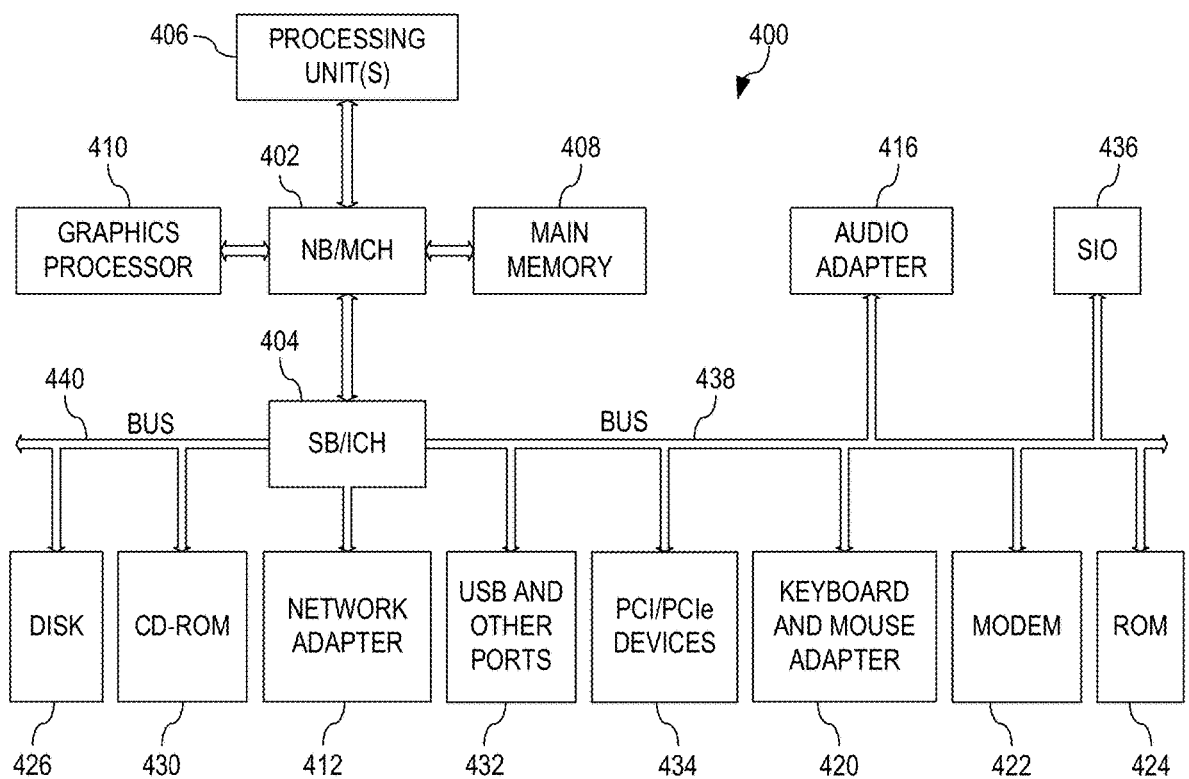
FIG. 4 is a block diagram of an example data processing system in which aspects of the illustrative embodiments are implemented.

As noted above, the mechanisms of the illustrative embodiments are rooted in the computer technology arts and are implemented using logic present in such computing or data processing systems. These computing or data processing systems are specifically configured, either through hardware, software, or a combination of hardware and software, to implement the various operations described above. As such, FIG. 4 is provided as an example of one type of data processing system in which aspects of the present invention may be implemented. Many other types of data processing systems may be likewise configured to specifically implement the mechanisms of the illustrative embodiments.

FIG. 4 is a block diagram of an example data processing system in which aspects of the illustrative embodiments are implemented. Data processing system 400 is an example of a computer, such as a server 304A-D or client 310-712 in FIG. 3, in which computer usable code or instructions implementing the processes for illustrative embodiments of the present invention are located. In one illustrative embodiment, FIG. 4 represents a server computing device, such as a server 304A, which, which implements a cognitive system 300 and medical image viewer application 330, where the server 304A further is specifically configured and executes hardware and/or software logic to implement the semi-supervised GAN classification system 320 of FIG. 3.

In the depicted example, data processing system 400 employs a hub architecture including North Bridge and Memory Controller Hub (NB/MCH) 402 and South Bridge and Input/Output (I/O) Controller Hub (SB/ICH) 404. Processing unit 406, main memory 408, and graphics processor 410 are connected to NB/MCH 402. Graphics processor 410 is connected to NB/MCH 402 through an accelerated graphics port (AGP).

In the depicted example, local area network (LAN) adapter 412 connects to SB/ICH 404. Audio adapter 416, keyboard and mouse adapter 420, modem 422, read only memory (ROM) 424, hard disk drive (HDD) 426, CD-ROM drive 430, universal serial bus (USB) ports and other communication ports 432, and PCI/PCIe devices 434 connect to SB/ICH 404 through bus 438 and bus 440. PCI/PCIe devices may include, for example, Ethernet adapters, add-in cards, and PC cards for notebook computers. PCI uses a card bus controller, while PCIe does not. ROM 424 may be, for example, a flash basic input/output system (BIOS).

HDD 426 and CD-ROM drive 430 connect to SB/ICH 404 through bus 440. HDD 426 and CD-ROM drive 430 may use, for example, an integrated drive electronics (IDE) or serial advanced technology attachment (SATA) interface. Super I/O (SIO) device 436 is connected to SB/ICH 404.

An operating system runs on processing unit 406. The operating system coordinates and provides control of various components within the data processing system 400 in FIG. 4. As a client, the operating system is a commercially available operating system such as Microsoft® Windows 10®. An object-oriented programming system, such as the Java™ programming system, may run in conjunction with the operating system and provides calls to the operating system from Java™ programs or applications executing on data processing system 400.

As a server, data processing system 400 may be, for example, an IBM® eServer™ System p° computer system, running the Advanced Interactive Executive (AIX®) operating system or the LINUX® operating system. Data processing system 400 may be a symmetric multiprocessor (SMP) system including a plurality of processors in processing unit 406. Alternatively, a single processor system may be employed.

Instructions for the operating system, the object-oriented programming system, and applications or programs are located on storage devices, such as HDD 426, and are loaded into main memory 408 for execution by processing unit 406. The processes for illustrative embodiments of the present invention are performed by processing unit 406 using computer usable program code, which is located in a memory such as, for example, main memory 408, ROM 424, or in one or more peripheral devices 426 and 430, for example.

A bus system, such as bus 438 or bus 440 as shown in FIG. 4, is comprised of one or more buses. Of course, the bus system may be implemented using any type of communication fabric or architecture that provides for a transfer of data between different components or devices attached to the fabric or architecture. A communication unit, such as modem 422 or network adapter 412 of FIG. 4, includes one or more devices used to transmit and receive data. A memory may be, for example, main memory 408, ROM 424, or a cache such as found in NB/MCH 402 in FIG. 4.

Those of ordinary skill in the art will appreciate that the hardware depicted in FIGS. 3 and 4 may vary depending on the implementation. Other internal hardware or peripheral devices, such as flash memory, equivalent non-volatile memory, or optical disk drives and the like, may be used in addition to or in place of the hardware depicted in FIGS. 3 and 4. Also, the processes of the illustrative embodiments may be applied to a multiprocessor data processing system, other than the SMP system mentioned previously, without departing from the spirit and scope of the present invention.

Moreover, the data processing system 400 may take the form of any of a number of different data processing systems including client computing devices, server computing devices, a tablet computer, laptop computer, telephone or other communication device, a personal digital assistant (PDA), or the like. In some illustrative examples, data processing system 400 may be a portable computing device that is configured with flash memory to provide non-volatile memory for storing operating system files and/or user-generated data, for example. Essentially, data processing system 400 may be any known or later developed data processing system without architectural limitation.

Figure 5:
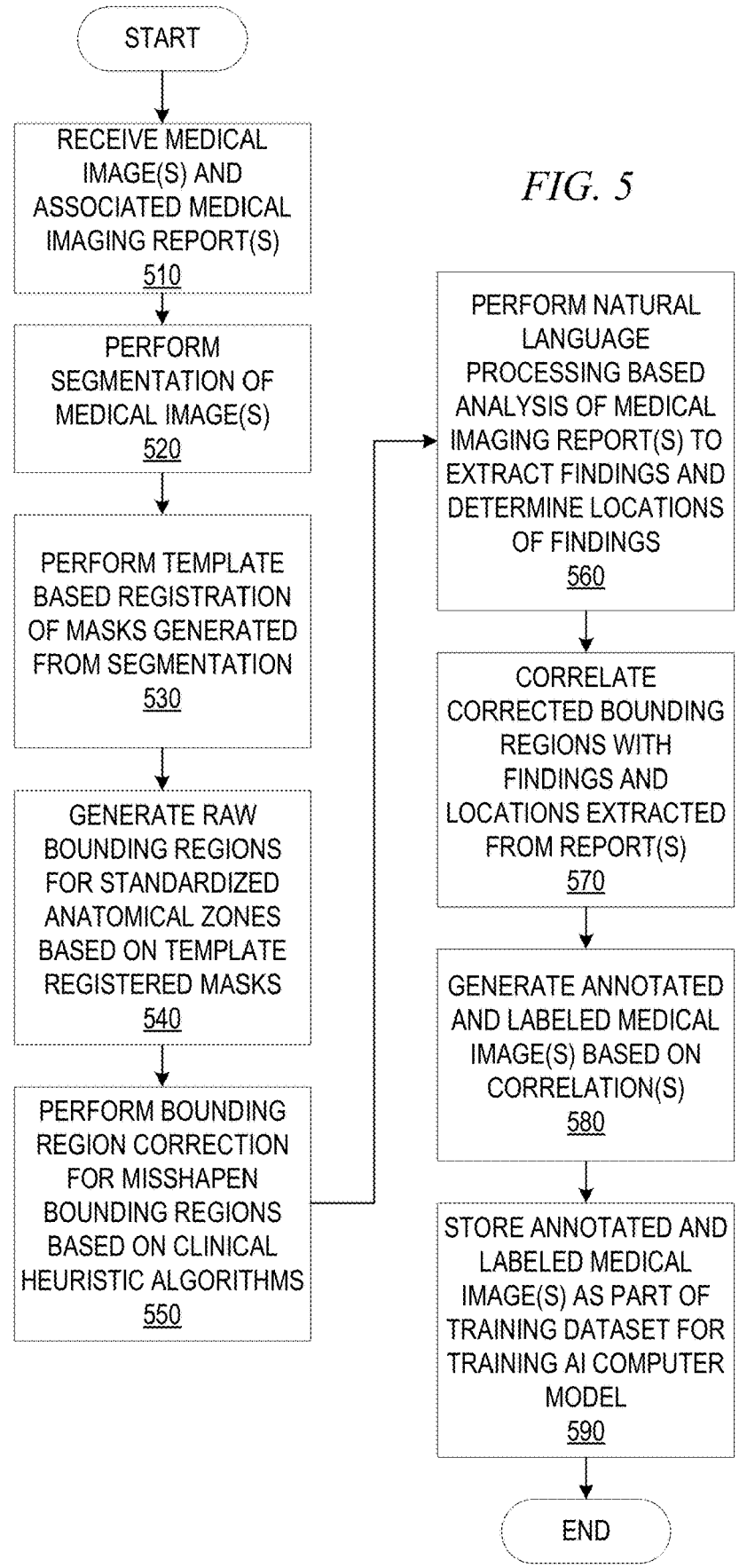
FIG. 5 is a flowchart outlining an example operation for performing automatic medical image annotation and labeling for generating a training dataset to train an artificial intelligence computing system in accordance with one illustrative embodiment.

FIG. 5 is a flowchart outlining an example operation for performing automatic medical image annotation and labeling for generating a training dataset to train an artificial intelligence computing system in accordance with one illustrative embodiment. The operation outlined in FIG. 5 may be performed by the AMIAL pipeline system described previously, for example, as part of a process for generating a training dataset for training an AI/cognitive computing system. The outlined operation, for ease of description, will be described as being performed for a single input medical image. It should be appreciated that the process may be performed for multiple input medical images as well. In the case of multiple medical images, the outlined operation may be repeated for each medical image, or each operation may be performed for each medical image at substantially a same time, such as in parallel or as in a batch processing or the like. While FIG. 5 outlines a process for generating a training dataset using the AMIAL pipeline system mechanisms, this operation may likewise be used for medical image viewing or the like. For example, in such a medical viewing application, rather than the final step of storing the annotated and labeled medical image as part of the training dataset, the annotated and labeled medical image may be output via a medical image viewer application or the like.

As shown in FIG. 5, the operation starts by receiving a medical image and associated medical imaging report (step 510). Segmentation is performed on the medical image (step 520) and template registration of the resulting masks generated by the segmentation is performed to generate template registered masks (step 530). Raw bounding regions for the standardized anatomical zones are generated based on the template registered masks (step 540). Correction of the raw bounding regions is performed for any misshapen bounding regions, using clinical heuristic algorithms (step 550). The result is that a final set of corrected bounding region annotations of the original input medical image are generated and associated with the medical image.

Thereafter, or even in a parallel operation to the image analysis of steps 510-550, the medical imaging report is processed using natural language process to extract finding and location information for these findings, such as using the ontology and/or vocabulary and mapping rules described above (step 560). The resulting anomaly labels and locations are correlated with the final set of corrected bounding region annotations generated in step 550 (step 570). Based on these correlations, an automatically annotated and labeled medical image is generated (step 580). The automatically generated annotated and labeled medical image is then stored as part of a training dataset for training an AI computer model (step 590). The operation then terminates.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising at least one processor and at least one memory, the method comprising:

automatically segmenting an input image of a subject into one or more segments, at least by processing the input image through a machine learning trained artificial neural network computer model trained to identify the one or more segments in input images, to generate a mask corresponding to recognized internal structures of the subject, wherein the machine learning trained artificial neural network computer model is trained based on normal input images in which no anomalies are present in the normal input images;

generating a template data structure based on an input set of annotated images, wherein the template data structure specifies standardized internal structure zones of the subject;

automatically registering the mask with the template data structure to generate a template registered mask identifying standardized internal structure zones present within the mask;

automatically generating bounding region annotations for each standardized internal structure zone present in the template registered mask;

automatically correlating the bounding region annotations with labels indicating whether or not the bounding region comprises an anomaly in the input image based on an analysis of a received natural language text description of the input image; and automatically storing the bounding region annotations and labels in association with the input image to provide an automatically annotated and labeled image data structure.

2. The method of claim 1, wherein the subject is a human being, the input image is a medical image of an anatomical region of the human being, and the internal structures of the subject are anatomical structures within a body of the human being.

3. The method of claim 1, wherein generating the template data structure based on the input set of annotated images comprises:

receiving a set of annotated input images comprising boundary region annotations specifying internal structure zones of corresponding subjects in corresponding annotated input images of the set of annotated input images; and performing a registration operation on the set of annotated input images to generate the template data structure specifying standardized internal structure zones based on the boundary region annotations in the set of annotated input images.

4. The method of claim 1, wherein automatically generating bounding region annotations for each standardized internal structure zone present in the template registered mask comprises performing an affine transformation on the template registered mask to predict coordinates in the input image for the contour boundaries of the standardized internal structure zones identified in the template registered mask.

5. The method of claim 1, wherein automatically generating bounding region annotations for each standardized internal structure zone present in the template registered mask comprises:

generating a first set of bounding region annotations based on the standardized internal structure zones present in the template registered mask; and performing a bounding region correction operation on the first set of bounding region annotations based on an application of one or more heuristic algorithms to the first set of bounding region annotations to generate a second set of bounding region annotations, wherein the one or more heuristic algorithms correlate image features with bounding regions and ratios of dimensions of bounding regions.

6. The method of claim 1, wherein automatically correlating the bounding region annotations with labels further comprises:

performing computer executed natural language processing on the natural language text description of the image to extract from the natural language text description of the input image a reference to an anomaly;

correlating the reference to the anomaly with a standardized internal structure zone based on an ontology or anomaly-to-location mapping rule data structure;

identifying a bounding region annotation in the generated bounding region annotations corresponding to the standardized internal structure zone correlated with the reference to the anomaly; and associating a label of the anomaly with the identified bounding region.

7. The method of claim 1, wherein the automatically annotated and labeled image data structure is stored as part of a training dataset for training an artificial intelligence computing system to perform image analysis operations on other input images, and wherein the method further comprises performing a machine learning training of the artificial intelligence computing system based on the training dataset to generate a trained artificial intelligence computing system trained to perform image analysis of the other input images.

8. The method of claim 1, wherein:

the input image is one of a plurality of medical images of a portion of an anatomical structure of a plurality of human beings, the plurality of medical images are obtained from a medical image dataset repository based on an input specifying a medical image modality and portion of anatomical structure of interest; and the template data structure is one of a plurality of template data structures, and is specific to the modality and portion of anatomical structure of interest.

9. The method of claim 1, wherein the automatically annotated and labeled image data structure is provided to an image viewer application, and wherein the image viewer application renders the automatically annotated and labeled image data structure as a graphical image in which the bounding region annotations and labels are displayed.

10. A computer program product comprising a computer readable storage medium having a computer readable program stored therein, wherein the computer readable program, when executed on a data processing system, causes the data processing system to:

automatically segment an input image of a subject into one or more segments, at least by processing the input image through a machine learning trained artificial neural network computer model trained to identify the one or more segments in input images, to generate a mask corresponding to recognized internal structures of the subject, wherein the machine learning trained artificial neural network computer model is trained based on normal input images in which no anomalies are present in the normal input images;

generate a template data structure based on an input set of annotated images, wherein the template data structure specifies standardized internal structure zones of the subject;

automatically register the mask with the template data structure to generate a template registered mask identifying standardized internal structure zones present within the mask;

automatically generate bounding region annotations for each standardized internal structure zone present in the template registered mask;

automatically correlate the bounding region annotations with labels indicating whether or not the bounding region comprises an anomaly in the input image based on an analysis of a received natural language text description of the input image; and automatically store the bounding region annotations and labels in association with the input image to provide an automatically annotated and labeled image data structure.

11. The computer program product of claim 10, wherein the subject is a human being, the input image is a medical image of an anatomical region of the human being, and the internal structures of the subject are anatomical structures within a body of the human being.

12. The computer program product of claim 10, wherein the computer readable program further causes the data processing system to generate the template data structure based on the input set of annotated images at least by:

receiving a set of annotated input images comprising boundary region annotations specifying internal structure zones of corresponding subjects in corresponding annotated input images of the set of annotated input images; and performing a registration operation on the set of annotated input images to generate the template data structure specifying standardized internal structure zones based on the boundary region annotations in the set of annotated input images.

13. The computer program product of claim 10, wherein the computer readable program further causes the data processing system to automatically generate bounding region annotations for each standardized internal structure zone present in the template registered mask at least by performing an affine transformation on the template registered mask to predict coordinates in the input image for the contour boundaries of the standardized internal structure zones identified in the template registered mask.

14. The computer program product of claim 10, wherein the computer readable program further causes the data processing system to automatically generate bounding region annotations for each standardized internal structure zone present in the template registered mask at least by:

generating a first set of bounding region annotations based on the standardized internal structure zones present in the template registered mask; and performing a bounding region correction operation on the first set of bounding region annotations based on an application of one or more heuristic algorithms to the first set of bounding region annotations to generate a second set of bounding region annotations, wherein the one or more heuristic algorithms correlate image features with bounding regions and ratios of dimensions of bounding regions.

15. The computer program product of claim 10, wherein the computer readable program further causes the data processing system to automatically correlate the bounding region annotations with labels further at least by:

performing computer executed natural language processing on the natural language text description of the image to extract from the natural language text description of the input image a reference to an anomaly;

correlating the reference to the anomaly with a standardized internal structure zone based on an ontology or anomaly-to-location mapping rule data structure;

identifying a bounding region annotation in the generated bounding region annotations corresponding to the standardized internal structure zone correlated with the reference to the anomaly; and associating a label of the anomaly with the identified bounding region.

16. The computer program product of claim 10, wherein the automatically annotated and labeled image data structure is stored as part of a training dataset for training an artificial intelligence computing system to perform image analysis operations on other input images, and wherein the computer readable program further causes the data processing system to perform a machine learning training of the artificial intelligence computing system based on the training dataset to generate a trained artificial intelligence computing system trained to perform image analysis of the other input images.

17. The computer program product of claim 10, wherein:

the input image is one of a plurality of medical images of a portion of an anatomical structure of a plurality of human beings, the plurality of medical images are obtained from a medical image dataset repository based on an input specifying a medical image modality and portion of anatomical structure of interest; and the template data structure is one of a plurality of template data structures, and is specific to the modality and portion of anatomical structure of interest.

18. A data processing system comprising:

at least one processor; and at least one memory coupled to the at least one processor, wherein the at least one memory comprises instructions which, when executed by the at least one processor, cause the at least one processor to:

automatically segment an input image of a subject into one or more segments, at least by processing the input image through a machine learning trained artificial neural network computer model trained to identify the one or more segments in input images, to generate a mask corresponding to recognized internal structures of the subject, wherein the machine learning trained artificial neural network computer model is trained based on normal input images in which no anomalies are present in the normal input images;

generate a template data structure based on an input set of annotated images, wherein the template data structure specifies standardized internal structure zones of the subject;

automatically register the mask with the template data structure to generate a template registered mask identifying standardized internal structure zones present within the mask;

automatically generate bounding region annotations for each standardized internal structure zone present in the template registered mask;

automatically correlate the bounding region annotations with labels indicating whether or not the bounding region comprises an anomaly in the input image based on an analysis of a received natural language text description of the input image; and automatically store the bounding region annotations and labels in association with the input image to provide an automatically annotated and labeled image data structure.

* * * * *